United States Patent
Taub et al.

(12) 
(10) Patent No.: US 8,845,330 B2
(45) Date of Patent: *Sep. 30, 2014

(54) METHOD FOR PREPARING A PHYSICAL PLASTER MODEL

(71) Applicant: Cadent Ltd, Or Yehuda (IL)

(72) Inventors: Eldad Taub, Reut (IL); Avi Kopelman, Palo Alto, CA (US)

(73) Assignee: Cadent, Ltd., Or Yehuda (IL)

(\*) Notice: Subject to any disclaimer, the term of this patent is extended or adjusted under 35 U.S.C. 154(b) by 0 days.

This patent is subject to a terminal disclaimer.

(21) Appl. No.: 13/886,159

(22) Filed: May 2, 2013

(65) Prior Publication Data

US 2013/0246014 A1    Sep. 19, 2013

Related U.S. Application Data

(63) Continuation of application No. 11/714,857, filed on Mar. 7, 2007, now Pat. No. 8,454,364, which is a continuation of application No. 10/676,257, filed on Oct. 2, 2003, now Pat. No. 7,220,124.

(60) Provisional application No. 60/422,782, filed on Oct. 31, 2002, provisional application No. 60/415,931, filed on Oct. 3, 2002.

(51) Int. Cl.
*A61C 11/00* (2006.01)

(52) U.S. Cl.
USPC ........................................... 433/213

(58) Field of Classification Search
USPC .................. 433/213–214, 54–67; 700/97–98, 700/118–120; 703/1; 382/154, 128, 293, 382/294; 264/17–18

See application file for complete search history.

(56) References Cited

U.S. PATENT DOCUMENTS

| 2,138,254 | A |   | 11/1938 | Mink |       |
|-----------|---|---|---------|------|-------|
| 2,621,406 | A | * | 12/1952 | McPhee | 433/55 |
| 4,315,740 | A | * | 2/1982  | Mercer et al. | 433/63 |
| 4,521,188 | A | * | 6/1985  | Metzler | 433/74 |
| 4,573,917 | A |   | 3/1986  | Erickson |  |
| 5,569,033 | A | * | 10/1996 | Michael | 433/74 |
| 5,611,686 | A | * | 3/1997  | Silva | 433/74 |
| 5,788,489 | A | * | 8/1998  | Huffman | 433/60 |

(Continued)

FOREIGN PATENT DOCUMENTS

| DE | 395385 C    | 5/1924 |
|----|-------------|--------|
| DE | 3541891 A1  | 6/1987 |

(Continued)

OTHER PUBLICATIONS

European search report and opinion dated Oct. 1, 2012 for EP Application No. 12159572.2.

*Primary Examiner* — Yogesh Patel

(74) *Attorney, Agent, or Firm* — Wilson Sonsini Goodrich & Rosati

(57) ABSTRACT

The invention provides a method for creating a physical teeth model. The method comprises the following steps: providing a virtual three dimensional (3D) representation of a patient's dentition that comprises at least a region of the teeth that includes a tooth stump on which a crown is to be fitted or a region on to which a bridge is to be fitted; and preparing a physical model of the jaws of a subject from a blank, based on information from said virtual 3D image.

21 Claims, 3 Drawing Sheets

(56) References Cited

U.S. PATENT DOCUMENTS

| | | |
|---|---|---|
| 6,322,359 B1 | 11/2001 | Jordan et al. |
| 6,431,871 B1 * | 8/2002 | Luthardt .................. 433/223 |
| 7,220,124 B2 | 5/2007 | Taub et al. |
| 7,942,671 B2 | 5/2011 | Taub et al. |
| 8,454,364 B2 | 6/2013 | Taub et al. |
| 2002/0013636 A1 | 1/2002 | O'Brien et al. |
| 2002/0015934 A1 | 2/2002 | Rubbert et al. |
| 2002/0048741 A1 | 4/2002 | Jordan et al. |
| 2002/0064759 A1 * | 5/2002 | Durbin et al. ............ 433/213 |
| 2002/0081554 A1 * | 6/2002 | Marshall et al. .......... 433/213 |
| 2002/0150859 A1 | 10/2002 | Imgrund et al. |
| 2002/0164556 A1 | 11/2002 | Huffman |
| 2003/0012423 A1 | 1/2003 | Boland et al. |
| 2003/0124492 A1 * | 7/2003 | Perot ....................... 433/213 |
| 2004/0172150 A1 | 9/2004 | Perot et al. |
| 2004/0197740 A1 * | 10/2004 | Amar ...................... 433/214 |
| 2011/0183294 A1 | 7/2011 | Taub et al. |

FOREIGN PATENT DOCUMENTS

| | | |
|---|---|---|
| WO | WO 97/03622 A1 | 2/1997 |
| WO | WO 98/52493 A1 | 11/1998 |
| WO | WO 99/15100 A1 | 4/1999 |
| WO | WO 00/08415 A1 | 2/2000 |
| WO | WO 00/25677 A1 | 5/2000 |

* cited by examiner

METHOD FOR PREPARING A PHYSICAL PLASTER MODEL

CROSS-REFERENCE

This application is a Continuation of U.S. patent application Ser. No. 11/714,857, filed on Mar. 7, 2007, which is a Continuation of U.S. patent application Ser. No. 10/676,257, filed on Oct. 2, 2003, now U.S. Pat. No. 7,220,124, which claims priority from U.S. Provisional Patent Application No. 60/422,782, filed on Oct. 31, 2002, and U.S. Provisional Patent Application No. 60/415,931, filed on Oct. 3, 2002, the entire contents of each of which are hereby incorporated by reference in their entirety.

FIELD OF THE INVENTION

This invention relates to the field of dentistry and in particular to a method of preparing plaster models for use in orthodontics, prosthodontics and other aspects of dental medicine.

BACKGROUND OF THE INVENTION

For a dentist or a dental technician, one of the main difficulties in making a working physical model of the teeth, including the inter-occlusal relationship between the jaws (also known by the term "master cast" or "working cast"), lies in respecting the position of a patient's artificial jaws when the teeth are in Centric Occlusion position. Separate molding of the upper and the lower teeth followed by the manual articulation of the two parts is a constant source of error. The precision of the cast depends on several factors, including, inter alia, the accuracy of the impressions and wax bites, the material from which the cast is constructed, and the identification of the anatomic. In addition, traditional methods using pins do not prevent linear expansion of the cast. This can result in the deformation of the new teeth that do not correspond perfectly to the original. Thus, the more precisely the working cast reproduces the anatomy of the mouth, the more accurate will be the spatial position, and the static and dynamic relationships. This provides a better possibility of producing a biomechanically acceptable restoration.

In order to reproduce with high precision the mechanical equivalent of functional and non-functional movements within the mouth, articulators (also known by the term "occluding devices") have been and still are under development. The articulators are used to precisely hold models of a patient's upper and lower teeth, so a dentist can study their bite or make a restoration.

Articulators are primarily used when a crown needs to be prepared. According to current practice, after diagnosing in a patient the need for a crown or a bridge, the dentist cuts the tooth to be reconstructed by the crown or bridge and prepares two impressions and a wax bite of the patient's jaws. One impression is of the area prepared for the crown and the surrounding area. The other impression is of the opposite jaw. A wax bite is used to record the spatial relation between the jaws at occlusion. Based on the impressions, wax bite and written instructions of the dentist, a technician prepares in a lab the corresponding plaster jaws which are trimmed and mounted on an articulator. Using the wax bites, the spatial relation between the jaws is determined. At this stage, the tooth within the preparation to be reconstructed is temporarily separated from the plaster so that the area with the anatomic information (the area defining the anatomic contour) and the finish line are exposed. The finish line is typically marked manually by the lab technician in ink on the preparation and a crown is built based on the resulting preparation. The quality of the crown prepared is examined by placing the crown on the preparation in the articulator and verifying that there is a good occlusion of the crown with the opposite teeth. If in the affirmative, the crown is sent to the dentist for placement on the preparation in the patient's mouth.

SUMMARY OF THE INVENTION

The present invention concerns a unique method of preparing a physical working teeth model of teeth, e.g. a model made of hard plaster, used for the fabrication of orthodontics and prosthodontics Crown or Bridges. The method utilizes a three dimensional (3D) virtual image of the patient's dentition or parts of it. Based on digital data representing said 3D image, a physical 3D teeth model is constructed.

The term "teeth model" will be used to denote a physical, three-dimensional representation of teeth in a solid matrix having a surface relief corresponding to the teeth arrangement of the individual. Such a model may be a "positive teeth model", comprising a teeth replica, namely, a model where each tooth is represented by a projection or bulge having contours identical in size and shape to the corresponding tooth; or a "negative teeth model", where each tooth is represented by a cavity or recess with contours identical in size, but opposite in shape to the contours of the corresponding tooth.

Thus, according to one embodiment, the invention provides a method for preparing a physical positive working model of a patient's dentition. According to another embodiment, the invention provides a method for preparing a physical negative model from which a positive working model can be fabricated, according to known dentistry procedures.

The method of the invention is of particular use in the construction of crowns or bridges. Thus, according to the invention, the 3D virtual image comprises at least the region of the teeth that includes a tooth stump on which a crown is to be fitted or a region on to which a bridge is to be fitted. Based on the virtual image of the dentition, a physical model of the two jaws is prepared. Thereafter, the resulting model, being positive or negative, as the case may be, is used for a variety of purposes, for example to prepare a crown, a bridge or other dental appliance; to analyze the relationship between the upper and lower jaws; to show the patient the crown or bridge; etc.

Alternatively, the virtual image may be further manipulated and based on the digital data representing the image, a virtual crown or bridge is constructed. Based on the virtual image of the crown or bridge, a physical model of the crown or bridge is prepared.

A virtual three-dimensional (3D) image is obtained e.g. in the manner as described in PCT publication No. WO97/03622 or PCT publication No. WO00/08415.

The dentist (or the technician, as the case may be) may construct a virtual image of the patient's dentition either with or without the virtual image of the crown or bridge, and then may send such data to the lab technician. There, a physical model may be prepared, e.g. by milling, 3D lithography or by any other appropriate means, according to said data. The physical model prepared by the technician can be sent to the dentist, for his approval (the physical model can also be fabricated at the dentist's office).

The physical model has typically one member that represents the upper jaw and another that represents the lower jaw. It order to render it easy to match these two members to one another, they may be produced with markings or appropriate physical alignment arrangement for aligning the jaws to represent the alignment of the jaws of the patient. Said data that includes the virtual image thus preferably includes also data bits for producing such markings or arrangement.

Markings may be in the form of depressions or protrusions on the face of the members that are made such so as to provide the technician with a tool for the proper alignment of the two members. A physical alignment arrangement may include a mounting arrangement for mounting the two members to an articulator to yield a proper occlusion alignment. By another example, the physical alignment arrangement may include one or more alignment reference components in one member that once fitted with one or more corresponding components in the other member, ensure proper alignment of the two members.

Thus, the present invention provides a dental articulator that precisely simulates the occlusion relationship of the jaws as well as the three-dimensional movement of a human jaw.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

As is true in any method of making a physical model, e.g. a plaster model of a patient's dentition, it is most important to start with an accurate representation of the jaws and teeth and the inter-occlusal relationship between the jaws. For this purpose, the instant invention relies on a virtual model of the patient's dentition.

Digital data representing a virtual teeth model may be obtained by a variety of methods, such as that described in PCT Application No. PCT/IL96/00036 (publication No. WO97/03622) and in PCT Application No. PCT/IL99/00431 (publication No. WO00/08415). The virtual three-dimensional image may be manipulated, for example, in a manner described in PCT Application No. PCT/IL99/00577 (publication No. WO00/25677). In particular, the virtual three-dimensional (3D) image is obtained by utilizing a physical negative teeth model, e.g. a negative teeth model that comprises the teeth impression by means of an impression matrix. The physical negative teeth model may be used as such, thus providing digital negative representation of the patient's dentition, from which a digital positive representation of the patient's dentition may be digitally obtained.

Alternatively, the physical negative teeth model may be used to prepare a physical positive teeth model, from which a digital positive teeth representation is provided. After the virtual image is generated, the display is typically a computerized display, provided with software permitting the technician to visualize the virtual image from different angles. As will be appreciated, the invention is not limited to any specific display means and any means for presenting the image such as, for example, in a printed format, on a computer display screen, etc., may be employed in accordance with the invention.

In most situations, the dentist will take three virtual impressions. One impression is of the preparation area for the crown, bridge or other dental appliances, along with the surrounding teeth. Another impression is of the teeth on the opposite jaw. The third impression records the spatial relationship between and the spacing of the two jaws in a centric occlusion. This information from the virtual impressions is placed in a 3D file that contains the two jaws and the spatial relationship between them in occlusion. Thereafter, the 3D file may be transferred to the laboratory.

Figure 1:
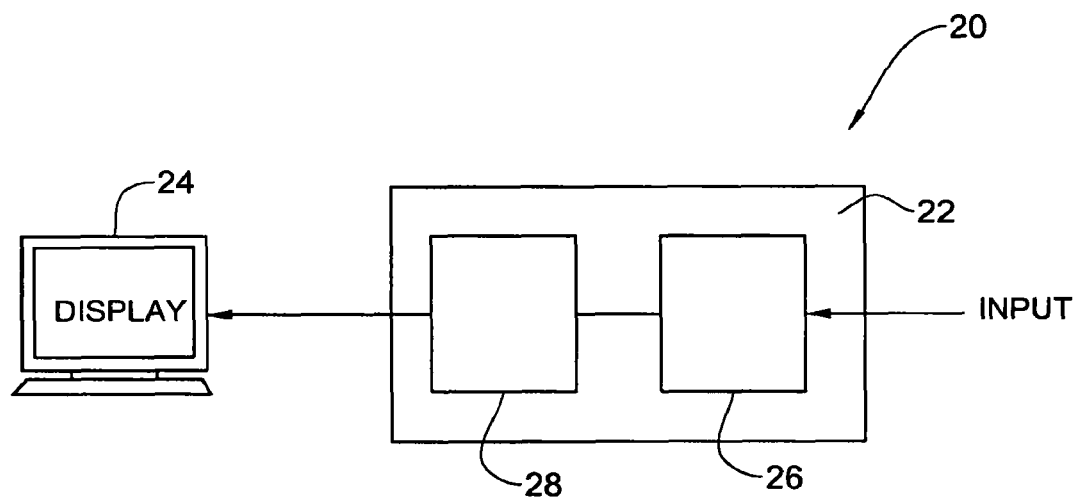
FIG. 1 shows, by way of a block diagram, a computerized device for constructing a virtual impression of the patient's dentition.

Reference is made to FIG. 1 showing a computerized device generally designated 20 including a processor 22 and a display unit 24. Running in the processor 22 is a first software utility 26 that receives an input of a three dimensional virtual teeth model and then processes, automatically or through the user, manipulable software utility 28, to construct a three dimensional virtual teeth model that includes the region that is to be treated, which can then be fed for display to display unit 24. By this means, the virtual impression of the dentition is made and the information may then be stored. The technician may then simulate any treatment area on the computer. For example, the cutout in the tooth for the crown can be simulated, along with fitting of the crown.

Figure 2:
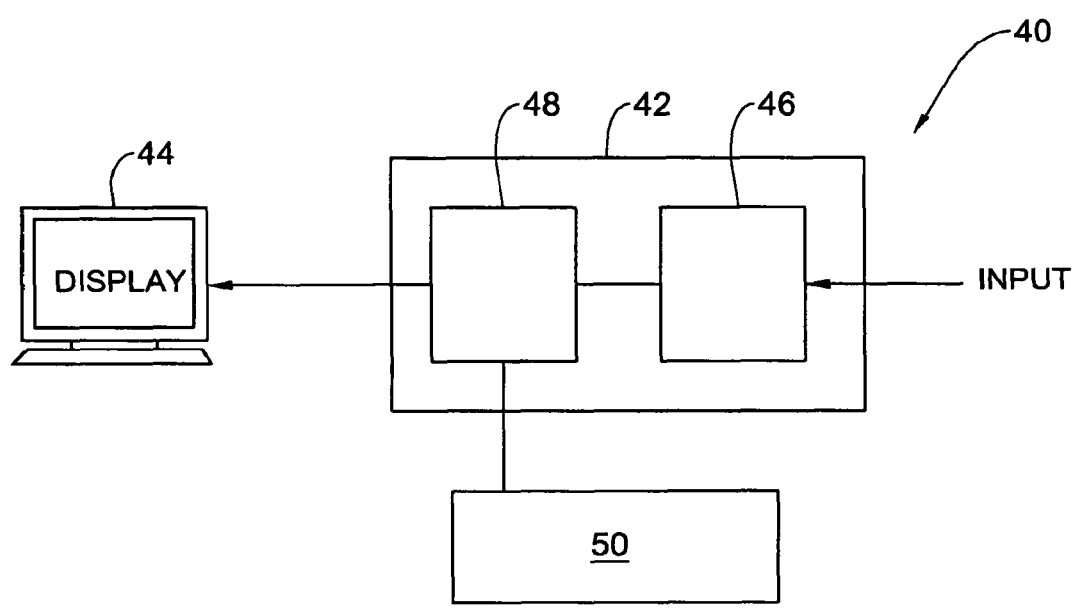
FIG. 2 shows, by way of a block diagram, a computerized device for milling a plaster model, based on the information from the virtual impression, in accordance with an embodiment of the invention.

Reference is now being made to FIG. 2 showing a system generally designated 40. In FIG. 2, like components to those shown in FIG. 1, are given the same reference numerals shifted by 20 (namely component 42, for example, is 30 functionally identical to component 22 in FIG. 1). System 40 of FIG. 2 includes an apparatus 50 that is used to construct a physical model utilizing digital data received from software utility 48. For this purpose, a Computer Numerical Control (CNC) milling machine 50 may be used. However, the invention is not limited to the use of a CNC machine and any other CAM (Computer Aided Manufacturing) technology that can produce a physical model out of virtual data may be used.

To manufacture a crown, a bridge, or any dental appliance, the lab technician requires two physical jaws models mounted on an articulator or placed in the correct spatial orientation one against the other. According to this method, the information for the two jaws and their spatial relationship in occlusion is in a digital 3D file. Alternatively, or in addition, the proper occlusion may be determined in a manner disclosed in WO 98/52493. The computer guided milling (or other technology) machine is connected to the computer with the 3D file of the virtual impression, and then a physical model of each one of the jaws is milled from a blank made of plaster, or other appropriate material taking into consideration also the spatial relation between the two jaws and their occlusion. At this point, the technician has his necessary physical model and can proceed with making the crown or the bridge.

Based on information from the virtual 3D image, the dentist or a technician may generate a 3D model of a crown to be fitted on a tooth stump or of a bridge to be fitted on the tooth surface, to generate a digital file on which basis the lab technician, through the use of a computer driven milling machine, may generate a physical crown, bridge or other dental appliances.

Figure 3:
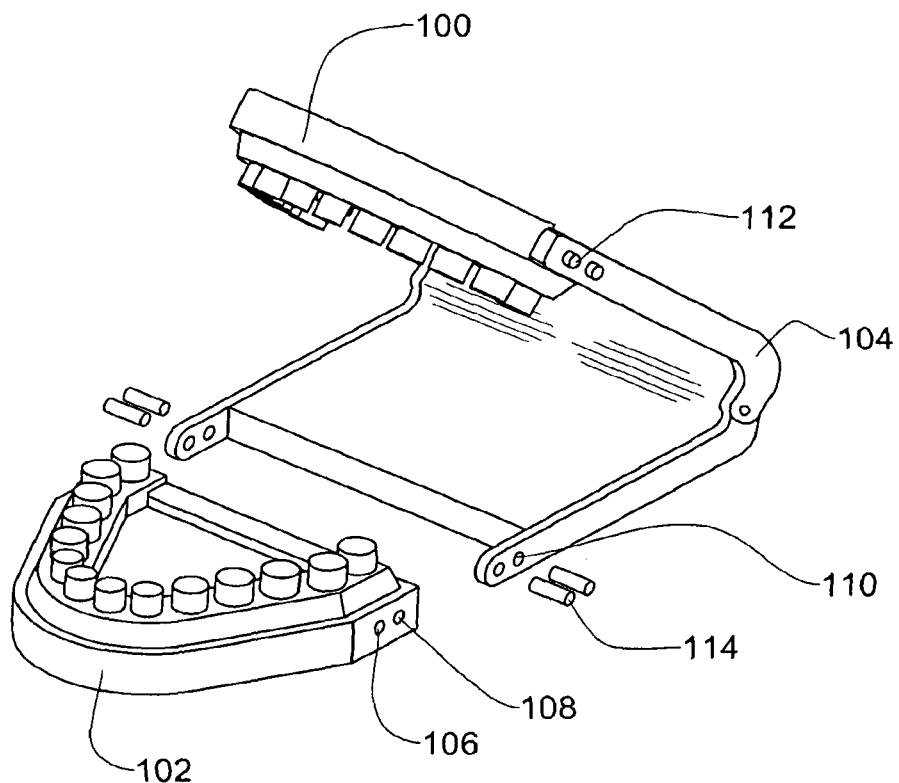
FIG. 3 shows a perspective view of the plaster model arranged on an articulator.

It should be noted that the physical model generated by device 40 might be a positive model or alternatively, a negative model. FIG. 3 shows plaster cast members 100 and 102 fabricated according to the invention and representing the upper and lower jaws, respectively. The members 100 and 102 can be mounted on an articulator 104 to simulate the proper occlusion relation. For that both members have articulator engagement portions 106 with reference holes 108 that can be registered with holes 110 engagement bit 112 of articulator 104, which engagement is through pins 114. The engagement portion 106 with the reference holes 108, are initially defined in the virtual 3D image. In this model the proper inter jaw occlusion are first defined, as explained above, and after the proper inter jaw occlusion is determined, the virtual 3D model may be virtually combined with an articulator to define the articulator-engagement portion with its reference holes.

This is then included in the digital file used to produce the plaster model. The reference holes may be produced automatically by the milling machine. However, the reference holes may be difficult to produce by the milling machine and may need to be produced after milling, as a separate step, for example, based on markings produced automatically during the milling procedure.

Figure 4:
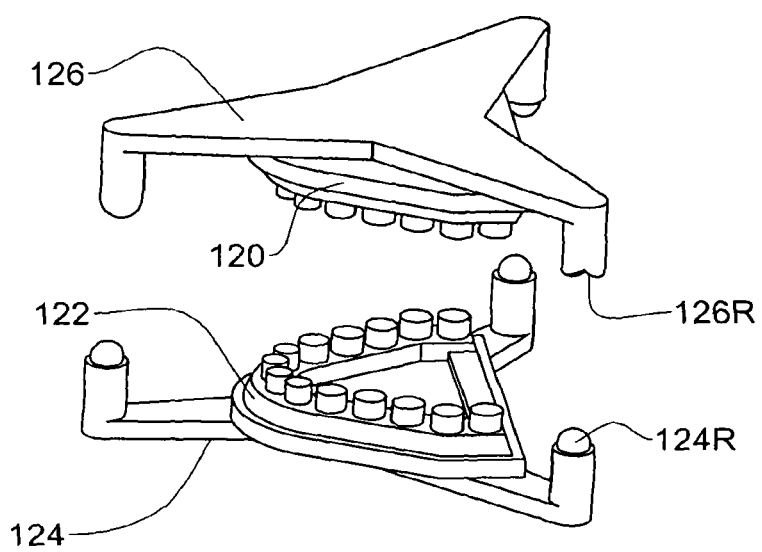
FIG. 4 shows a perspective view of the plaster model with references for aligning the jaws.

Reference is now made to FIG. 4 that shows another embodiment of a manner for proper alignment of the two cast members. The two cast members 120 and 122 are produced each with a corresponding aligning structures 124 and 126. Each of these aligning structures includes positioning reference components 124R and 126R, respectively, the former having an end abutment, that fits into a matching recess in the latter. This alignment structure is first produced virtually after virtual alignment of the two jaw members and thereafter structures 124 and 126 may then be added. The data file prepared from the virtual model and that is utilized for manufacture of the physical members 120 and 122, this includes, according to this embodiment, also data for integral production of said structures.

As may be appreciated, the lab technician has to build a crown, a bridge, or other dental appliances, that will have a good fit on the prepared area of the tooth. Contact with the surrounding teeth must be good, and such as in the case of crowns, there must also be correct contact with teeth on the opposing jaw. If the crown does not fit correctly, the bite will be affected and the crown will not fit comfortably in the mouth. The articulator is used to mount the model, so the crown and be formed and properly fitted. This is why the model must be highly accurate, or the crown will not fit correctly in the patient's mouth. It is from this information that an accurate 3D file of the dentition is created, and the milling of the plaster physical mold is based on the information in this 3D file. Due to the enhanced accuracy of the information about the dentition, the physical model can be made more accurately, thereby leading to a more accurate manufacture of the crown.

Figure 5:
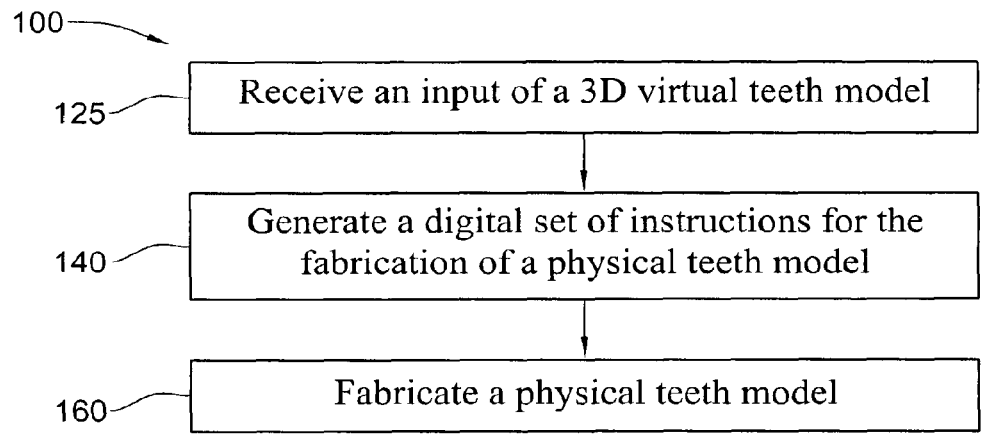
FIG. 5 shows, by way of a flow chart, a method for fabricating a physical teeth model, in accordance with an embodiment of the invention.

Reference is now being made to FIG. 5, and the reader is referred to FIG. 2 for a complete understanding of their function. Illustrated in FIG. 5 are the main steps 100 in a method of the invention for the fabrication of a physical teeth model utilizing the device 40 and a CAM machine (CNC milling machine 50, in this example) connectable to the device 40, as shown in FIG. 2.

At step 125, the device 40 receives an input of a 3D virtual teeth model (constituting a 3D representation of a patient's dentition), and based on which, generates, at 140, digital information for the fabrication of a physical teeth model. Then at step 160, the machine 50 fabricates the physical teeth model.

It should be noted that additional steps might be needed and carried out manually or automatically, e.g., for the generation of additional digital information, which can be displayed by the display utility 24, as previously explained. It should also be noted that the machine 50 does not need to be part of the device 40 and can be a separate utility. In the later case, the digital information generated by the device 40 is transmitted to the machine 50 via a direct connection (through wires or wireless communication means) or via a communication network (e.g. the Internet).

According to the common CAD techniques, soft materials such as wax may be used for the fabrication of the physical model. However, the fabricated physical model made of such relative soft materials is easily deformable by mechanical stresses. This outcome is highly undesirable in the context of dentistry, in which a positive working model is used, for example for the creation of orthodontic or prosthodontics appliances. Any deformation in the fabricated positive model degrades the precision of the appliance based on the positive model, as well as degrades the quality of the orthodontics and prosthodontics treatment.

The present invention, by one of its embodiment, solves the above problem by providing a method for the fabrication of a precise negative model, from which a positive working model can then be produced, for example from a hard plaster, by utilizing traditional dentistry procedures.

Figure 6:
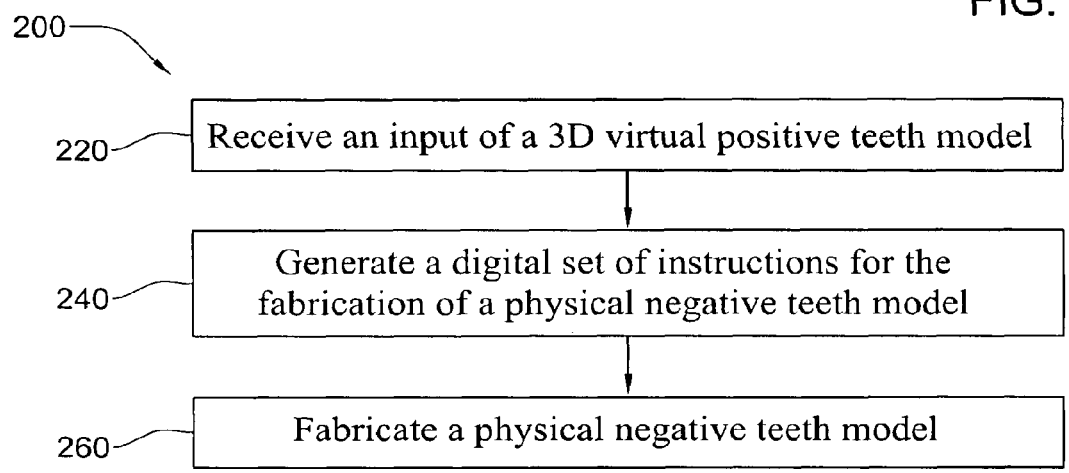
FIG. 6 and FIG. 7 illustrate two specific examples, respectively, of the method of FIG. 5.
Figure 7:
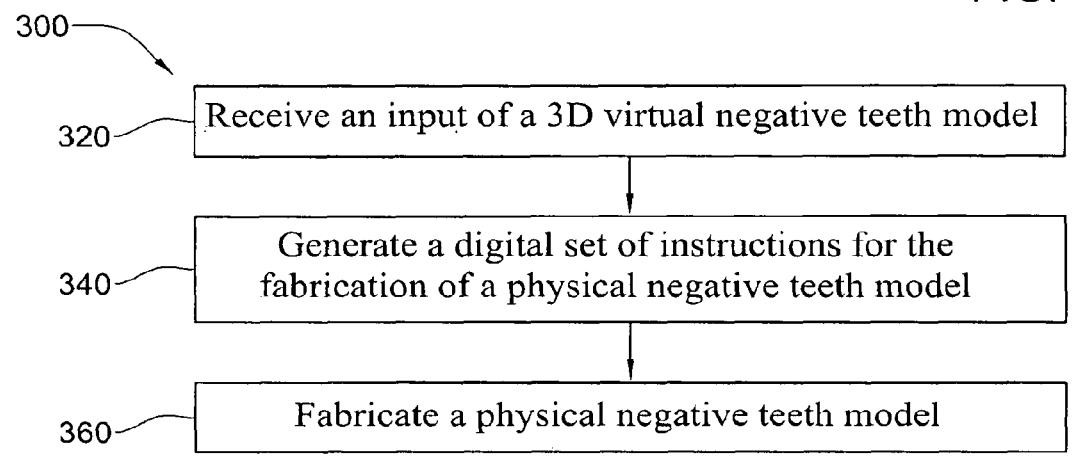

FIG. 6 and FIG. 7 more specifically illustrate flow diagrams 200 and 300 (respectively) for the fabrication of a negative teeth model utilizing the method of FIG. 5. In the example of FIG. 6, the device 40 receives an input of a 3D virtual positive teeth model (step 220), and generates digital information for the fabrication of a physical negative teeth model (step 240). The machine 50, being a part of or connectable to the device 40, operates to fabricate the physical negative teeth model (step 260). At a later stage (not shown), the fabricated physical negative teeth model is used for the fabrication of a positive working model, according to known procedures, e.g. by filling the negative cast with a hard plaster and removing the negative cast.

In the example of FIG. 7, the device 40 receives an input of a 3D virtual negative teeth model (step 320). The processing of this data for the generation of the digital information for the fabrication of the physical negative teeth model (at step 340) might not need the generation of a digital positive model. However, an additional step (not shown) can be carried out between steps 320 and 340, in which a digital positive model, from which the information is derived, is generated.

As mentioned above, the fabricated physical model can bear marking or articulator engagement portions, for proper relations. When a negative model is fabricated, it bears a negative marking and/or engagement portions (e.g. depressions), thus providing the positive working model with positive marking and/or engagement portions (e.g. corresponding protrusions).

It should be noted that a dedicated device could implement the procedures 100, 200 and 300. Alternatively, these procedures can be integrated with other computerized dentistry methods, e.g. virtual treatment plan and the like.

While some preferred embodiments have been shown and illustrated, it is to be understood by a skilled person that it is not intended thereby to limit the disclosure, but rather it is intended to cover all modifications and arrangements falling within the spirit and scope of the present invention.

What is claimed is:

1. A system for generating a digital model of teeth, comprising:
   a processor operably coupled to a computer readable storage medium comprising instructions which, when executed, cause the processor to:
   (a) receive a three dimensional (3D) virtual model of a patient's dentition including
       (1) virtual dental surfaces including a region including at least one dental preparation, and
       (2) virtual model components corresponding to at least a part of each upper and lower jaw of the patient's dentition;
       receive 3D data representative of at least the spatial relationship between the upper and lower jaws in occlusion;
   (b) incorporate in the 3D virtual model, one or more digitally created structural reference components comprising a first structure of the upper jaw that couples together with a second structure of the lower jaw so as to define an alignment arrangement for the 3D virtual model based on the 3D data, thereby defining an updated 3D virtual model, the one or more digitally created structural reference components configured to provide virtual occlusion alignment between the virtual model components according to the spatial relationship; and
   (c) following step (a), output data for preparing a physical three dimensional (3D) model, the data including the virtual model components that respectively represent physical model components based on the updated 3D virtual model obtained in step (a), wherein the physical model components include one or more physical structural reference components respectively corresponding to the one or more digitally created structural reference components to enable selectively providing physical occlusion alignment between the physical model components corresponding to the virtual occlusion alignment.

2. The system according to claim 1, wherein the data includes instructions for a computer driven machine to prepare the physical model components.

3. The system according to claim 1, wherein the data includes a 3D data file comprising updated 3D virtual model data for 3D lithography manufacturing.

4. The system according to claim 1, wherein the virtual model components include the upper jaw and the lower jaw of the patient's dentition, the upper jaw and/or the lower jaw having markings to guide for proper alignment of the upper and lower jaw.

5. The system according to claim 1, wherein the virtual model components include the upper jaw and the lower jaw of the patient's dentition, the upper jaw and/or the lower jaw having an alignment arrangement to permit proper occlusion alignment of the upper and lower jaw.

6. The system according to claim 5, wherein the alignment arrangement includes a mounting arrangement for mounting the physical model components on an articulator.

7. The system according to claim 6, wherein the mounting arrangement comprises articulator engagement portions formed in the upper and/or lower jaw, the articulator engagement portions comprising reference holes configured to engage with respect to corresponding holes or pins in the articulator, wherein the articulator engagement portions and the reference holes are defined in the 3D virtual model.

8. The system according to claim 5, wherein the alignment arrangement includes one or more alignment reference components in the upper and lower jaw such that the alignment reference component in the upper jaw fits with the corresponding alignment reference component in the lower jaw to yield proper alignment of the upper and lower jaw.

9. The system according to claim 1, wherein the data further comprises instructions for manufacturing a crown or a bridge to be fitted on the dental preparation.

10. The system according to claim 9, the instructions further causing the computer to generate a 3D model of a crown or bridge to be fitted on the dental preparation based on information from the 3D virtual model.

11. The system according to claim 10, wherein the data further comprises instructions for a CAM machine to prepare a physical crown or bridge based on the 3D model of the crown or bridge.

12. The system according to claim 9, wherein the data further comprises instructions for a computer driven 3D lithography machine to make a physical model of the region that includes the at least one dental preparation, the physical model including a tooth stump on which a crown is to be fitted, and a physical model of the crown to be fitted on the tooth stump.

13. The system according to claim 9, wherein the data further comprises instructions for a computer driven 3D lithography machine to make a physical model of the region of the teeth on which a bridge is to be fitted, and a physical model of the bridge to be fitted on the dental preparation.

14. The system according to claim 1, wherein the updated 3D virtual model further includes data representative of the upper and lower jaws.

15. The system according to claim 1, wherein the virtual alignment arrangement comprises an articulator engagement portion in the 3D virtual model, the articulator engagement portion being defined by virtually combining the 3D virtual model with a virtual articulator.

16. A system for generating a digital model of teeth, comprising:
   a processor operably coupled to a computer readable storage medium comprising instructions which, when executed, cause the processor to:
   (a) receive a three dimensional (3D) virtual model of a patient's dentition including virtual model components corresponding to at least a part of each upper and lower jaw thereof and comprising virtual dental surfaces;
   (b) receive 3D data representative of at least the spatial relationship between the upper and lower jaws in occlusion;
   (c) define a virtual alignment arrangement by incorporating in said 3D virtual model one or more virtual structural reference components comprising a first structure of the upper jaw that couples together with a second structure of the lower jaw so as to define an alignment arrangement for said 3D virtual model based on said 3D data, thereby defining an updated 3D virtual model, said one or more virtual structural reference components configured to provide virtual occlusion alignment between said virtual model components according to the spatial relationship; and
   (d) following step (a), output data for preparing a positive physical three dimensional (3D) model, the data including virtual model components representing physical model components based on said updated 3D virtual model obtained in step (a), wherein the physical model components include one or more physical structural reference components corresponding to the one or more virtual structural reference components to enable selectively providing physical occlusion alignment of the physical 3D model corresponding to the virtual occlusion alignment.

17. The system according to claim 16, wherein the updated 3D virtual model further includes data representative of said jaws.

18. The system according to claim 16, wherein the virtual alignment arrangement comprises an articulator engagement portion in the 3D virtual model, the articulator engagement portion being defined by virtually combining the 3D virtual model with a virtual articulator.

19. The system according to claim 16, wherein the virtual alignment arrangement comprises articulator engagement portions formed in the upper and/or lower jaw, the articulator engagement portions comprising reference holes configured to engage with respect to corresponding holes or pins in the articulator, wherein the articulator engagement portions and the reference holes are defined in the 3D virtual model.

20. The system according to claim 16, wherein the virtual alignment arrangement includes one or more alignment reference components in the upper and lower jaw such that the alignment reference component in the upper jaw fits with the corresponding alignment reference component in the lower jaw to yield proper alignment of the upper and lower jaw.

21. A method for generating a digital model of teeth, the method comprising:
  (a) receiving, by a computer system, a three dimensional (3D) virtual model of a patient's dentition including
    (1) virtual dental surfaces including a region including at least one dental preparation, and
    (2) virtual model components corresponding to at least a part of each upper and lower jaw of the patient's dentition;
  (b) receiving, by the computer system, 3D data representative of at least the spatial relationship between the upper and lower jaws in occlusion;
  (c) incorporating in the 3D virtual model, using the computer system, one or more digitally created structural reference components comprising a first structure of the upper jaw that couples together with a second structure of the lower jaw so as to define an alignment arrangement for the 3D virtual model based on the 3D data, thereby defining an updated 3D virtual model, the one or more digitally created structural reference components configured to provide virtual occlusion alignment between the virtual model components according to the spatial relationship; and
  (d) following step (a), outputting data, from the computer system, for preparing a physical three dimensional (3D) model, the data including the virtual model components that respectively represent physical model components based on the updated 3D virtual model obtained in step (a), wherein the physical model components include one or more physical structural reference components respectively corresponding to the one or more digitally created structural reference components to enable selectively providing physical occlusion alignment between the physical model components corresponding to the virtual occlusion alignment.

* * * * *